United States Patent [19]

Howell et al.

[11] Patent Number: 4,705,766

[45] Date of Patent: Nov. 10, 1987

[54] MIXTURE OF A MOLYBDENUM CARBOXYLATE AND A MOLYBDENUM DITHIOPHOSPHATE OR A MOLYBDENUM DITHIOCARBAMATE FOR USE IN A HYDROVISBREAKING PROCESS

[75] Inventors: Jerald A. Howell; Simon G. Kukes, both of Bartlesville, Okla.

[73] Assignee: Phillips Petroleum Company, Bartlesville, Okla.

[21] Appl. No.: 866,552

[22] Filed: May 23, 1986

Related U.S. Application Data

[62] Division of Ser. No. 677,134, Nov. 30, 1984, Pat. No. 4,608,152.

[51] Int. Cl.[4] .......................... B01J 31/04; B01J 31/12
[52] U.S. Cl. .................................... 502/167; 502/162; 502/170

[58] Field of Search ............... 502/162, 167, 155, 170, 502/211; 252/32.7 E, 33.3

[56] References Cited

U.S. PATENT DOCUMENTS 4,191,658  3/1980  Jahnke ........................... 252/32.7 E
4,528,108  7/1985  Grover ........................... 252/32.7 E Primary Examiner—W. J. Shine
Attorney, Agent, or Firm—French and Doescher

[57] ABSTRACT

A decomposable molybdenum compound selected from the group consisting of a mixture of a molybdenum dithiophosphate and a molybdenum carboxylate and a mixture of a molybdenum dithiocarbamate and a molybdenum carboxylate is disclosed. The decomposable molybdenum compound may be added, in a hydrovisbreaking process, to a hydrocarbon-containing feed stream prior to contacting the feed stream with hydrogen under suitable hydrovisbreaking conditions.

17 Claims, No Drawings

MIXTURE OF A MOLYBDENUM CARBOXYLATE AND A MOLYBDENUM DITHIOPHOSPHATE OR A MOLYBDENUM DITHIOCARBAMATE FOR USE IN A HYDROVISBREAKING PROCESS

This application is a division of application Ser. No. 677,134, which was filed on Nov. 30, 1984, now U.S. Pat. No. 4,608,152.

This invention relates to a hydrovisbreaking process for hydrocarbon-containing feed streams, which substantially minimizes carbon formation. In one aspect, this invention relates to a process for removing metals from a hydrocarbon-containing feed stream. In another aspect, this invention relates to a process for removing sulfur or nitrogen from a hydrocarbon-containing feed stream. In still another aspect, this invention relates to a process for removing potentially cokeable components from a hydrocarbon-containing feed stream. In still another aspect, this invention relates to a process for reducing the amount of heavies in a hydrocarbon-containing feed stream.

It is well known that crude oil as well as products from extraction and/or liquefaction of coal and lignite, products from tar sands, products from shale oil and similar products may contain components which make processing difficult. As an example, when these hydrocarbon-containing feed streams contain metals such as vanadium, nickel and iron, such metals tend to concentrate in the heavier fractions such as the topped crude and residuum when these hydrocarbon-containing feed streams are fractionated. The presence of the metals make further processing of these heavier fractions difficult since the metals generally act as poisons for catalysts employed in processes such as catalytic cracking, hydrogenation or hydrodesulfurization.

The presence of other components such as sulfur and nitrogen is also considered detrimental to the processability of a hydrocarbon-containing feed stream. Also, hydrocarbon-containing feed streams may contain components (referred to as Ramsbottom carbon residue) which are easily converted to coke in processes such as catalytic cracking, hydrogenation or hydrodesulfurization. It is thus desirable to remove components such as sulfur and nitrogen and components which have a tendency to produce coke.

It is also desirable to reduce the amount of heavies in the heavier fractions such as the topped crude and residuum. As used herein the term heavies refers to the fraction having a boiling range higher than about 1000° F. This reduction results in the production of lighter components which are of higher value and which are more easily processed.

Hydrofining is a broad term used to describe a process to remove components such as metals, sulfur, nitrogen and Ramsbottom carbon residue from a hydrocarbon containing feed stream and to reduce the amount of heavies in the hydrocarbon containing feed stream. Hydrovisbreaking is a type of hydrofining and is generally characterized by a heat soak in the presence of hydrogen. Other hydrofining processes may contact the hydrocarbon containing feed stream with a fixed catalyst bed.

A number of different hydrovisbreaking processes are known. Some of these processes employ decomposable molybdenum compounds such as molybdenum hexacarbonyl, molybdenum naphthenate and molybdenum octoate. The decomposable molybdenum compound is mixed with the hydrocarbon containing feed stream and the hydrocarbon containing feed stream, which also contains molybdenum, is heated in the presence of hydrogen under suitable hydrovisbreaking conditions.

A major problem with prior hydrovisbreaking processes and particularly those which employ decomposable molybdenum compounds has been the formation of coke, which is extremely undesirable because of the loss of valuable hydrocarbon products. It is thus an object of this invention to provide a hydrovisbreaking process in which the production of coke is reduced with respect to previous hydrovisbreaking processes which employed the decomposable molybdenum compounds referred to above.

In accordance with the present invention, at least one decomposable molybdenum additive selected from the group consisting of a mixture of a molybdenum dithiophosphate and a molybdenum carboxylate and a mixture of a molybdenum dithiocarbamate and a molybdenum carboxylate is mixed with a hydrocarbon-containing feed stream in a hydrovisbreaking process. The hydrocarbon-containing feed stream, which also contains molybdenum, is heated in the presence of hydrogen under suitable hydrovisbreaking conditions. After being processed in such a manner, the hydrocarbon-containing feed stream will contain a significantly reduced concentration of metals, sulfur, nitrogen and Ramsbottom carbon residue as well as a reduced amount of heavy hydrocarbon components and only relatively small amounts of dispersed coke particles. Removal of these components from the hydrocarbon-containing feed stream in this manner provides an improved processability of the hydrocarbon-containing feed stream in processes such as catalytic cracking, hydrogenation or further hydrodesulfurization. Use of a molybdenum additive selected from the group consisting of a mixture of a molybdenum dithiophosphate and a molybdenum carboxylate and a mixture of molybdenum dithiocarbamate and a molybdenum carboxylate results in improved suppression of coke formation with respect to the use of molybdenum compounds such as molybdenum hexacarbonyl or molybdenum naphthenate and molybdenum octoate alone.

Other objects and advantages of the invention will be apparent from the foregoing brief description of the invention and the appended claims as well as the detailed description of the invention which follows.

Any suitable hydrocarbon-containing feed stream may be processed using the above described catalyst composition in accordance with the present invention. Suitable hydrocarbon-containing feed streams include petroleum products, coal, pyrolyzates, products from extraction and/or liquefaction of coal and lignite, products from tar sands, products from shale oil and similar products. Suitable hydrocarbon feed streams include full range (untopped) crudes, gas oil having a boiling range from about 205° C. to about 538° C., topped crude having a boiling range in excess of about 343° C. and residuum. However, the present invention is particularly directed to heavy feed streams such as heavy full range crudes, heavy topped crudes and residuum and other materials which are generally regarded as too heavy to be distilled. These materials will generally contain the highest concentrations of metals, sulfur, nitrogen and Ramsbottom carbon residues.

It is believed that the concentration of any metal in the hydrocarbon-containing feed stream can be reduced in accordance with the present invention. However, the present invention is particularly applicable to the removal of vanadium, nickel and iron.

The sulfur which can be removed in accordance with the present invention will generally be contained in organic sulfur compounds. Examples of such organic sulfur compounds include sulfides, disulfides, mercaptans, thiophenes, benzylthiophenes, dibenzylthiophenes, and the like.

The nitrogen which can be removed in accordance with the present invention will also generally be contained in organic nitrogen compounds. Examples of such organic nitrogen compounds include amines, diamines, pyridines, quinolines, porphyrins, benzoquinolines and the like.

Any suitable molybdenum dithiophosphate compound may be used in the molybdenum additive. Generic formulas of suitable molybdenum dithiophosphates are:

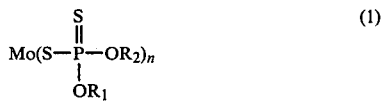 (1)

wherein $n=3, 4, 5, 6$; $R_1$ and $R_2$ are either independently selected from H, alkyl groups having 1-20 carbon atoms, cycloalkyl or alkylcycloalkyl groups having 3-22 carbon atoms and aryl, alkylaryl or cycloalkylaryl groups having 6-25 carbon atoms; or $R_1$ and $R_2$ are combined in one alkylene group of the structure

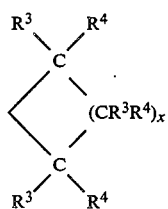

With $R^3$ and $R^4$ being independently selected from H, alkyl, cycloalkyl, alkylcycloalkyl and aryl, alkylaryl and cycloalkylaryl groups as defined above, and x ranging from 1 to 10.

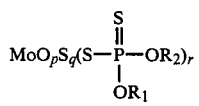 (2)

wherein
$p=0, 1, 2$; $q=0, 1, 2$; $(p+q)=1, 2$;
$r=1, 2, 3, 4$ for $(p+q)=1$ and
$r=1, 2$ for $(p+q)=2$;

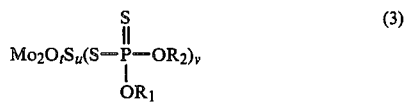 (3)

wherein
$t=0, 1, 2, 3, 4$; $u=0, 1, 2, 3, 4$;
$(t+u)=1, 2, 3, 4$
$v=4, 6, 8, 10$ for $(t+u)=1$; $v=2, 4, 6, 8$ for $(t+u)=2$;
$v=2, 4, 6$ for $(t+u)=3$, $v=2, 4$ for $(t+u)=4$.

Sulfurized oxomolybdenum (V) O,O'-di(2-ethylhexyl)-phosphorodithioate of the formula $Mo_2S_2O_2[S_2\cdot P(OC_8H_{17})_2]$ is particularly preferred.

Any suitable molybdenum dithiocarbamate compound may be used in the molybdenum additive. Generic formulas of suitable molybdenum (III), (IV), (V) and (VI) dithiocarbamates are:

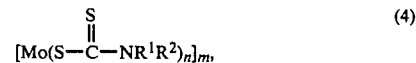 (4)

wherein $n=3, 4, 5, 6$; $m=1, 2$; $R^1$ and $R^2$ are either independently selected from H, alkyl groups having 1-20 carbon atoms, cycloalkyl groups having 3-22 carbon atoms and aryl groups having 6-25 carbon atoms; or $R^1$ and $R^2$ are combined in one alkylene group of the structure

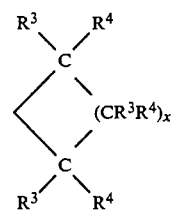

with $R^3$ and $R^4$ being independently selected from H, alkyl, cycloalkyl and aryl groups as defined above, and x ranging from 1 to 10.

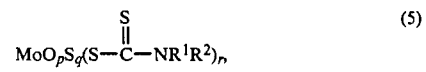 (5)

wherein
$p=0, 1, 2$; $q=0, 1, 2$; $(p+q)=1, 2$;
$r=1, 2, 3, 4$ for $(p+q)=1$ and
$r=1, 2$ for $(p+q)=2$;

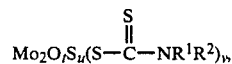 (6)

wherein
$t=0, 1, 2, 3, 4$; $u=0, 1, 2, 3, 4$;
$(t+u)=1, 2, 3, 4$
$v=4, 6, 8, 10$ for $(t+u)=1$; $v=2, 4, 6, 8$ for $(t+u)=2$;
$v=2, 4, 6$ for $(t+u)=3$, $v=2, 4$ for $(t+u)=4$.

Molybdenum(V) di(tridecyl)dithiocarbamate is particularly preferred.

Any suitable molybdenum carboxylate compound may be used in the molybdenum additive. Suitable molybdenum carboxylate compounds include aliphatic, cycloaliphatic and aromatic carboxylates having 1-20 carbon atoms. Preferred molybdenum carboxylates are molybdenum octoate and molybdenum naphthenate.

Any suitable concentration of the molybdenum carboxylate compound may be utilized in the mixture of molybdenum dithiophosphate and molybdenum carboxylate and the mixture of molybdenum dithiocarbamate and molybdenum carboxylate. The concentration of molybdenum carboxylate in the mixtures will generally be in the range of about 10 to about 90 weight percent and will more preferably be in the range of about 30 to about 70 weight percent. Since the dithiocarbamates and dithiophosphates are generally more expensive than the carboxylates, preferably the concentration of the carboxylates is increased to the extent possible. However, since the dithiocarbamates and dithiophosphates are more effective at reducing coke formation than the carboxylates, the desired reduction in coke formation must also be considered in the determining what concentration of the carboxylate to include in the molybdenum additive.

A major benefit of the present invention is the reduced cost of the additive with respect to the use of either the dithiocarbamate or dithiophosphate alone. This is particularly true in view of the fact that this reduced cost is achieved without the reduced performance in coke formation suppression which would be expected.

Any suitable concentration of the molybdenum additive may be added to the hydrocarbon-containing feed stream. In general, a sufficient quantity of the additive will be added to the hydrocarbon-containing feed stream to result in a concentration of molybdenum metal in the range of about 1 to about 1000 ppm and more preferably in the range of about 3 to about 300 ppm.

It is noted that one of the particular advantages of the present invention is the very small concentrations of molybdenum which may be used. This substantially improves the economic viability of the process.

The hydrovisbreaking process can be carried out by means of any suitable apparatus whereby there is achieved a contact of the hydrocarbon containing feed stream, the decomposable molybdenum compound and hydrogen under suitable hydrovisbreaking conditions. The hydrovisbreaking process can be carried out as a continuous process or as a batch process. The hydrovisbreaking process is in no way limited to the use of any particular type of process or apparatus.

The molybdenum additive may be combined with the hydrocarbon-containing feed stream in any suitable manner. The molybdenum additive may be mixed with the hydrocarbon-containing feed stream as a solid or liquid or may be dissolved in a suitable solvent (preferably an oil) prior to introduction into the hydrocarbon-containing feed stream. Any suitable mixing time may be used. However, it is believed that simply injecting the molybdenum additive into the hydrocarbon-containing feed stream is sufficient. No special mixing equipment or mixing period are required.

In a continuous process, the molybdenum additive is mixed with the hydrocarbon containing feed stream prior to introducing the hydrocarbon containing feedstream into the reactor. For a batch process, it is also generally more convenient to add the molybdenum additive to the hydrocarbon-containing feed stream before the hydrocarbon containing feed stream is introduced into the reactor and the reactor is pressurized with hydrogen gas. However, if desired, the molybdenum additive may be added to the hydrocarbon containing feed stream after the hydrocarbon containing feed stream is introduced into the batch reactor but before the hydrovisbreaking process is begun.

The pressure and temperature at which the molybdenum additive is introduced into the hydrocarbon-containing feed stream is not thought to be critical. However, a temperature above 100° C. is recommended.

Many hydrofining processes and some hydrovisbreaking processes are carried out using catalyst compositions. Such catalyst compositions generally comprise a support such as alumina, silica or silica/alumina. Catalyst compositions may also contain a promoter with typical promoters being the metals group VIB, group VIIB, and group VIII of the Periodic Table. Also, other types of catalyst may be used. The hydrovisbreaking process of the present invention is distinguished from hydrofining or hydrovisbreaking processes which employ catalyst compositions in that catalyst compositions are not employed in the hydrovisbreaking process of the present invention.

Any suitable reaction time in the hydrovisbreaking process may be utilized. In general, the reaction time will range from about 0.01 hours to about 10 hours. Preferably, the reaction time will range from about 0.1 to about 5 hours and more preferably from about 0.25 to about 3 hours. Thus, for a continuous process, the flow rate of the hydrocarbon containing feed stream should be such that the time required for the passage of the mixture through the reactor (residence time) will preferably be in the range of about 0.1 to about 5 hours and more preferably about 0.25 to about 3 hours. For a batch process, the hydrocarbon containing feed stream will preferably remain in the reactor for a time in the range of about 0.1 hours to about 5 hours and more preferably from about 0.25 hours to about 3 hours.

The hydrovisbreaking process can be carried out at any suitable temperature. The temperature will generally be in the range of about 250° C. to about 550° C. and will preferably be in the range of about 380° to about 480° C. Higher temperature do improve the removal of metals but temperatures should not be utilized which will have adverse effects on the hydrocarbon-containing feed stream, such as increased coking, and also economic considerations must be taken into account. Lower temperatures can generally be used for lighter feeds.

Any suitable hydrogen pressure may be utilized in the hydrovisbreaking process. The reaction pressure will generally be in the range of about atmospheric to about 10,000 psig. Preferably, the pressure will be in the range of about 500 to about 3,000 psig. Higher hydrogen pressures tend to reduce coke formation but operation at high pressure may have adverse economic consequences.

Any suitable quantity of hydrogen can be added to the hydrovisbreaking process. The quantity of hydrogen used to contact the hydrocarbon-containing feed stock, either in a continuous or batch process, will generally be in the range of about 100 to about 20,000 standard cubic feet per barrel of the hydrocarbon-containing feed stream and will more preferably be in the range of about 500 to about 5,000 standard cubic feet per barrel of the hydrocarbon-containing feed stream.

The following examples are presented in further illustration of the invention.

EXAMPLE I

In this example the experimental setup for batch-type hydrovisbreaking of heavy oils is described. About 100 grams of a topped (950° F.+) Hondo heavy crude (containing 18.2 weight-% Ramsbottom C, 6.2 weight-% S, 730 ppm (V+Ni), 0.55 weight-% xylene insolubles and a 1000° F.+ fraction of 85.1 weight-%) plus appropriate amounts of a decomposable molybdenum compound were added to a 300 cc stirred autoclave (Autoclave Engineers, Inc., Erie, PA), which was preheated to about 200° F. The unit was sealed, alternately pressured with $H_2$ and vented so as to eliminate air, and finally pressured with $H_2$ to the desired starting pressure (about 1400 psig). Stirring at about 1000 r.p.m. and rapid heating up to the test temperature about 800° F. was carried out. During the test run, hydrogen gas was added so as to maintain a constant pressure of about 2000–2300 psig at the final test temperature.

After heating at about 800° F. for about 60 minutes, the unit was cooled as quickly as possible, depressured and opened. The liquid product was collected and analyzed. Primarily, the amount of dispersed coke particles was determined (by filtration through a 0.45 μm membrane filter and weighing). Other test parameters were Ramsbottom carbon (ASTM D524), density of 60° F., xylene insoluble content and the amount of the 1000° F.+ fraction of the liquid product.

EXAMPLE II

This example illustrates the results of hydrovisbreaking tests in accordance with the procedure outlined in Example I. The following decomposable molybdenum compounds were tested:

A: Molyvan ® 807, a mixture of about 50 weight-% molybdenum (V) di(tridecyl)dithiocarbamate and about 50 weight-% of an aromatic oil (specific gravity: 0.963; viscosity at 210° F.: 38.4 SUS); Molyvan ® 807 contains about 4.6 weight-% Mo; it is marketed as an antioxidant and antiwear additive by R. T. Vanderbilt Company, Norwalk, CT;

B: Molyvan ® L, a mixture of about 80 weight-% of a sulfided molybdenum (V) dithiophosphate of the formula $Mo_2S_2O_2[PS_2(OR)_2]$ wherein R is the 2-ethylhexyl group, and about 20 weight-% of an aromatic oil (see above); marketed by R. T. Vanderbilt Company;

C: $Mo(CO)_6$, marketed by Aldrich Chemical Company, Milwaukee, Wis.,

D: Molybdenum (V) naphthenate, Mo salt of petroleum-derived saturated higher fatty acids; marketed by Shepherd Chemical Company, Cincinnati, Ohio.

E. Molybdenum (IV) octoate, $MoO(C_7H_{15}CO_2)_2$; containing about 8 weight-% Mo; marketed by Shepherd Chemical Company.

F: Phosphomolybdic acid, $20MoO_3.2H_3PO_4.48H_2O$; marketed by Fischer Scientific Company, Fairlawn, N.J.

Results are summarized in Table I.

TABLE I

| Run No. | Additives and Amounts | Coke Formation (Wt % of Feed) Measured | Coke Formation (Wt % of Feed) Predicted | % Conversion of 100° F.+ Fraction |
|---|---|---|---|---|
| 1 (Control) | A (50 ppm Mo) | 3.15 | — | 67.0 |
| 2 (Control) | E (50 ppm Mo) | 7.83 | — | 73.1 |
| 3 (Invention) | A (25 PPM Mo) + E (25 ppm Mo) | 2.60 | 5.5[1] | 60.6 |
| 4 (Control) | B (50 ppm Mo) | 4.06 | — | 65.5 |
| 2 (Control) | E (50 ppm Mo) | 7.83 | — | 73.1 |
| 5 (Invention) | B (25 ppm Mo) + E (25 ppm Mo) | 3.52 | 5.9[2] | 56.8 |
| 6 (Invention) | B (25 ppm Mo) + E (25 ppm Mo) | 4.87 | 5.9[2] | 80.8 |
| 7 (Invention) | B (25 ppm Mo) + E (50 ppm Mo) | 4.81 | — | 71.7 |
| 4 (Control) | B (50 ppm Mo) | 4.06 | — | 65.5 |
| 8 (Control) | D (50 ppm Mo) | 8.39 | — | 70.7 |
| 9 (Invention) | B (25 ppm Mo) + D (25 ppm Mo) | 4.30 | 6.2[3] | 64.4 |
| 4 (Control) | B (50 ppm Mo) | 4.06 | — | 65.5 |
| 10 (Control) | F (50 ppm Mo) | 7.16 | — | 63.6 |
| 11 (Control) | B (25 ppm Mo) + F (25 ppm Mo) | 5.53 | 5.6[4] | 62.4 |
| 4 (Control) | B (50 ppm Mo) | 4.06 | — | 65.5 |
| 12 (Control) | C (50 ppm Mo) | 8.88 | — | 68.9 |
| 13 (Control) | B (25 ppm Mo) + C (25 ppm Mo) | 6.49 | 6.5[5] | 69.9 |
| 14 (Control) | B (25 ppm Mo) | 6.24 | — | 66.5 |
| 15 (Control) | E (25 ppm Mo) | 10.23 | — | 75.8 |

[1] ½ (% coke in run 1 + % coke in run 2)
[2] ½ (% coke in run 4 + % coke in run 2)
[3] ½ (% coke in run 4 + % coke in run 8)
[4] ½ (% coke in run 4 + % coke in run 10)
[5] ½ (% coke in run 4 + % coke in run 12)

Data in Table I show that, unexpectedly, the hydrovisbreaking of the heavy oil feed with mixtures of molybdenum dithiocarbamate (compound A) and molybdenum octoate (compound E) produced less coke than runs with either A or E alone (compare runs 1, 2 and 3).

Similar results were obtained for mixtures of molybdenum dithiophosphate (compound B) and either molybdenum octoate (compound E) or molybdenum naphthenate (compound D). A comparison of runs 4, 2, 5 and 6 shows that, unexpectedly, the coke formation in runs with a mixture of B and E was less than what was predicted (from an arithmetic mean calculation using data from runs 4 and 2). A comparison of runs 4, 8 and 9 shows that the mixture of B and D also produced less coke than what was predicted (from an arithmetic mean calculation).

On the other hand, mixtures of molybdenum dithiophosphate with either phosphomolybdic acid (compound F) or with $Mo(CO)_6$ (compound C) did not produce the above-described beneficial effects (see runs 4, 8 11). A comparison of runs 2 and 4 with runs 14 and 15 shows that a reduction of the amount of added Mo substantially increased the formation of coke. Therefore, the observed effects of invention runs 3, 5–7 and 9 were not caused by the reduced amount of any of the added Mo compounds.

EXAMPLE III

In this example the experimental setup for the continuous hydrovisbreaking of heavy oils is described. A topped (650° F.+) Hondo heavy crude (containing 12.1 weight-% Ramsbottom C, 5.6 weight-% S, 480 ppm (Ni+V), a 1000° F.+ fraction of 62.0 weight-%, and having an API gravity of 9.0) plus, when desired, molybdenum compounds were stirred in a heated feed vessel. The oil feed was pumped at a rate of about 2 liters per hour into a stainless steel pipe of about ¼" inner diameter and was mixed with hydrogen gas (pressure:

1800 psig). The oil-gas mixture was heated to a temperature of almost 820° F. in a 60 feet long coiled stainless steel tube surrounded by an electric furnace and charged through an induction tube extending close to the bottom of a heated reactor (4 inch diameter and 26 inch length) where it mixed with the reactor contents. The product exited through an eduction tube, which was positioned so as to provide a liquid volume of about 1 liter and thus an average residence time of the oil-gas mixture of about 30 minutes at the reaction temperature of about 820° F.

The product passed through a pressure let-down valve into a series of phase separators and coolers. All liquid fractions were combined, and were analyzed as described in Example I. A tracer was introduced in the gaseous product stream. The tracer was analyzed in a gas chromatograph so as to calculate gas flows and hydrogen consumption. Results are summarized in Table II.

TABLE II

| Run No | 6 (Control) | 7 (Control) | 8 (Control) | 9 (Control) | 10 (Control) |
|---|---|---|---|---|---|
| Mo Additive | A | B | C | D | E |
| Mo Concentration (ppm) in Feed | 80 | 80 | 80 | 80 | 80 |
| Formed Coke (Wt % of Liquid Product) | 3.1 | 3.5 | 6.6 | 7.7 | 7.5 |
| Conversion of 1000° F.+ Fraction (%) | 53.4 | 54.6 | 60.4 | 59.1 | 59.9 |
| Gas Formation (SCF/bbl. of Oil Feed) | 265 | 254 | 292 | 304 | 312 |
| H$_2$ Consumption (SCF/bbl of Oil Feed) | 455 | 430 | 246 | 300 | 262 |

Based on these test results for molybdenum compounds A, B, C, D and E, it is believed that invention mixtures A+E, B+E and B+D can also be employed in continuous hydrovisbreaking operations and will exhibit the unexpectedly reduced coke formation shown by data in Table 1.

Reasonable variations and modifications are possible within the scope of the disclosure and the appended claims to the invention.

That which is claimed is:

1. A molybdenum containing mixture selected from the group consisting of a mixture comprising a molybdenum dithiophosphate and a molybdenum carboxylate and a mixture comprising a molybdenum dithiocarbamate and a molybdenum carboxylate.

2. A composition in accordance with claim 1 wherein said molybdenum containing mixture is a mixture comprising a molybdenum dithiophosphate compound and a molybdenum carboxylate compound.

3. A composition in accordance with claim 2 wherein said molybdenum dithiophosphate compound is selected from the group having the following generic formulas:

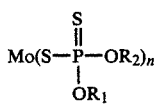
(1)

wherein
n=3, 4, 5, 6;

R$_1$ and R$_2$ are either independently selected from H, alkyl groups having 1-20 carbon atoms, cycloalkyl or alkylcycloalkyl groups having 3-22 carbon atoms and aryl, alkylaryl or cycloalkylaryl groups having 6-25 carbon atoms; or R$_1$ and R$_2$ are combined in one alkylene group of the structure

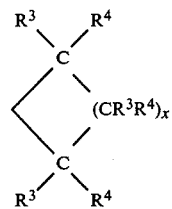

with R$^3$ and R$^4$ being independently selected from H, alkyl, cycloalkyl alkylcycloalkyl, aryl, alkylaryl and cycloalkylaryl groups as defined above, and x ranging from 1 to 10;

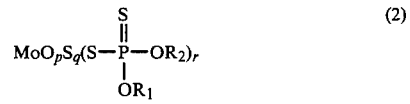
(2)

wherein
R$_1$ and R$_2$ are as previously defined in formula (1);
p=0, 1, 2; q=0, 1, 2; (p+q)=1, 2;
r=1, 2, 3, 4 for (p+q)=1 and
r=1, 2 for (p+q)=2;

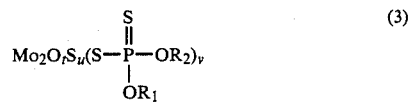
(3)

wherein
R$_1$ and R$_2$ are as previously defined in formula (1);
t=0, 1, 2, 3, 4; u=0, 1, 2, 3, 4;
(t+u)=1, 2, 3, 4
v=4, 6, 8, 10 for (t+u)=1; v=2, 4, 6, 8 for (t+u)=2;
v=2, 4, 6 for (t+u)=3, v=2, 4 for (t+u)=4.

4. A composition in accordance with claim 3 wherein said molybdenum dithiophosphate compound is oxymolybdenum (V) 0,0'-di(2-ethylhexyl)phosphorodithioate.

5. A composition in accordance with claim 2 wherein said molybdenum carboxylate compound is selected from the group consisting of alphatic, cyclo-aliphatic and aromatic carboxylates having 1-20 carbon atoms.

6. A composition in accordance with claim 5 wherein said molybdenum carboxylate compound is molybdenum octoate.

7. A composition in accordance with claim 5 wherein said molybdenum carboxylate is molybdenum naphthenate.

8. A composition in accordance with claim 2 wherein the concentration of said molybdenum carboxylate in said molybdenum containing mixture is in the range of about 10 to about 90 weight percent.

9. A composition in accordance with claim 2 wherein the concentration of said molybdenum carboxylate in said molybdenum containing mixture is in the range of about 30 to about 70 weight percent.

10. A composition in accordance with claim 1 wherein said molybdenum containing mixture is a mixture comprising a molybdenum dithiocarbamate compound and a molybdenum carboxylate compound.

11. A composition in accordance with claim 10 wherein said molybdenum dithiocarbamate compound is selected from the group having the following generic formulas:

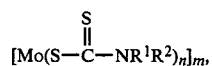 (1)

wherein
n=3, 4, 5, 6;
m=1, 2;
$R^1$ and $R^2$ are either independently selected from H, alkyl groups having 1–20 carbon atoms, cycloalkyl groups having 3–22 carbon atoms and aryl groups having 6–25 carbon atoms;
or $R^1$ and $R^2$ are combined in one alkylene group of the structure

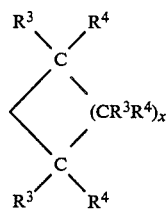

with $R^3$ and $R^4$ being independently selected from H, alkyl, cycloalkyl and aryl groups as defined above, and x ranging from 1 to 10;

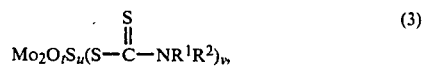 (2)

wherein
$R^1$ and $R^2$ are as previously defined in formula (1);
p=0, 1, 2; q=0, 1, 2; (p+q)=1, 2;
r=1, 2, 3, 4 for (p+q)=1 and
r=1, 2 for (p+q)=2

$$Mo_2O_tS_u(S-\overset{\overset{S}{\|}}{C}-NR^1R^2)_v \quad (3)$$

wherein
$R^1$ and $R^2$ are as previously defined in formula (1);
t=0, 1, 2, 3, 4; u=0, 1, 2, 3, 4;
(t+u)=1, 2, 3, 4
v=4, 6, 8, 10 for (t+u)=1; v=2, 4, 6, 8 for (t+u)=2;
v=2, 4, 6 for (t+u)=3, v=2, 4 for (t+u)=4.

12. A composition in accordance with claim 11 wherein said molybdenum dithiocarbamate compound is molybdenum (V) di(tridecyl)dithiocarbamate.

13. A composition in accordance with claim 10 wherein said molybdenum carboxylate compound is selected from the group consisting of aliphatic, cycloaliphatic and aromatic carboxylates having 1–20 carbon atoms.

14. A composition in accordance with claim 13 wherein said molybdenum carboxylate compound is molybdenum octoate.

15. A composition in accordance with claim 13 wherein said molybdenum carboxylate is molybdenum naphthenate.

16. A composition in accordance with claim 10 wherein the concentration of said molybdenum carboxylate in said molybdenum containing mixture is in the range of about 10 to about 90 weight percent.

17. A composition in accordance with claim 10 wherein the concentration of said molybdenum carboxylate in said molybdenum containing mixture is in the range of about 30 to about 70 weight percent.

* * * * *